US006602199B2

(12) United States Patent
Chen et al.

(10) Patent No.: US 6,602,199 B2
(45) Date of Patent: Aug. 5, 2003

(54) METHOD AND APPARATUS FOR MEASURING VALUES OF PHYSIOLOGICAL PARAMETERS

(75) Inventors: Yunquan Chen, Delta (CA); Anton Bogdan Zorn, Vancouver (CA); David Sholom Waterman, Delta (CA); Mark Elliot Gelfer, Vancouver (CA); Paul Richard Christensen, Burnaby (CA); Kevin Daryl Strange, Port Moody (CA)

(73) Assignee: VSM Technology Inc., Vancouver (CA)

( * ) Notice: Subject to any disclaimer, the term of this patent is extended or adjusted under 35 U.S.C. 154(b) by 140 days.

This patent is subject to a terminal disclaimer.

(21) Appl. No.: 09/988,110

(22) Filed: Nov. 19, 2001

(65) Prior Publication Data

US 2002/0035332 A1 Mar. 21, 2002

Related U.S. Application Data

(63) Continuation of application No. 09/328,432, filed on Jun. 9, 1999, now Pat. No. 6,332,867.

(51) Int. Cl.[7] .................................................. A61B 5/02
(52) U.S. Cl. ...................... 600/485; 600/490; 600/493; 600/494; 600/495; 600/496
(58) Field of Search ................................ 600/485, 490, 600/493–6, 500–503, 579, 561, 300

(56) References Cited

U.S. PATENT DOCUMENTS

| 4,349,034 A | 9/1982 | Ramsey, III |
| 4,360,029 A | 11/1982 | Ramsey, III |

(List continued on next page.)

FOREIGN PATENT DOCUMENTS

| EP | 0203181 B1 | 7/1992 |
| JP | 1032482 A | 2/1989 |
| JP | 1032845 | 2/1989 |
| JP | 1015118 | 6/1998 |

OTHER PUBLICATIONS

Staessen, J.A., Byttebier, G., Buntinx, F., Celis, H., O'Brien, E.T., and Fagard, R., "Antihypertensive Treatment Based on Conventional or Ambulatory Blood Pressure Measurement", Journal of American Medical Association, vol. 278, No. 13, pp. 1065–1072, 1997.

Joffres, M.R., Ghadirian, P., Fodor, J.G., Petrasovits, A., Chockalingam, A., and Hamet, P., "Awareness, Treatment, and Control of Hypertension in Canada", American Journal of Hypertension, vol. 10, pp. 1097–1102, 1997.

(List continued on next page.)

Primary Examiner—Robert L. Nasser
(74) Attorney, Agent, or Firm—Oyen Wiggs Green & Mutala (57) ABSTRACT

Apparatus for measuring a physiological parameter of a patient, such as blood pressure, takes a sequence consisting of a predetermined number of individual measurements. The apparatus computes a best estimate of the physiological parameter from values obtained in two or more of the measurements. The apparatus automatically takes a sequence of measurements and then stops. The apparatus can operate unattended so that it is not necessary for a physician or other health care worker to be present while measurements are being made. The use of the invention to measure blood pressure of a patient reduces the effect of "white coat" hypertension on the best estimate. Preferred embodiments of the apparatus ignore results of a first measurement in the sequence. The patient is already familiar with the apparatus when subsequent measurements are taken. This further reduces the possibility that the patient's reaction to the process of measurement will affect the results of the measurement.

75 Claims, 6 Drawing Sheets

U.S. PATENT DOCUMENTS

| | | |
|---|---|---|
| 4,404,974 A | 9/1983 | Titus |
| 4,592,365 A | 6/1986 | Georgi |
| 4,747,412 A | 5/1988 | Yamaguchi |
| 5,031,629 A | 7/1991 | DeMarzo |
| 5,201,320 A | 4/1993 | Barker |
| 5,280,790 A | 1/1994 | Brooks |
| 5,355,890 A | 10/1994 | Aguirre et al. |
| 5,505,206 A | 4/1996 | Walloch |
| 5,542,428 A | 8/1996 | Jayne |
| 5,590,662 A | 1/1997 | Hersh et al. |
| 5,606,977 A | 3/1997 | Ramsey, III et al. |
| 5,752,919 A | 5/1998 | Schrimpf |
| 5,758,652 A | 6/1998 | Nikolic |
| 5,830,149 A | 11/1998 | Oka et al. |
| 5,836,887 A | 11/1998 | Oka et al. |
| 6,036,361 A | 7/2000 | Gregory |
| 6,083,172 A | 7/2000 | Baker, Jr. et al. |
| 6,332,867 B1 * | 12/2001 | Chen et al. ............. 600/300 |

OTHER PUBLICATIONS

American Heart Association, "Recommendations for Human Blood Pressure Determination by Sphygmomanometers", Dallas: AHA, 1987.

Pickering, T.G., James, G.D., Boddie, C., Harshfield, G.A., Blank, S., and Laragh, J.H., "How Common is White Coat Hypertension?", Journal of American Medical Association, vol. 259, No. 2, pp. 225–228, 1988.

Watson, R.D.S., Lumb, R., Young, M.A., Stallard, T.J., Davies, P., and Littler, W.A., "Variation in Cuff Blood Pressure in Untreated Outpatients with Mild Hypertension—Implications for Initiating Antihypertensive Treatment", Journal of Hypertension, vol. 5, No. 2, pp. 207–211, 1987.

James, G.D., Pickering, T.G., Yee, L.S., Harshfield, G.A., Riva, S., and Laragh, J.H., "The Reproducibility of Average Ambulatory, Home, and Clinic Pressures", Hypertension, vol. 11, No. 6, Part 1, pp. 545–549, 1988.

White, W.B. Schulman, P.,McCabe, E.J., and Dey, H.M., "Average Daily Blood Pressure, Not Office Blood Pressure, Determines Cardiac Function in Patients With Hypertension", Journal of American Medical Association, vol. 261, No. 6, pp. 873–877, 1989.

* cited by examiner

METHOD AND APPARATUS FOR MEASURING VALUES OF PHYSIOLOGICAL PARAMETERS

This is a continuation of application Ser. No. 09/328,432, filed Jun. 9, 1999, now U.S. Pat. No. 6,332,867.

FIELD OF THE INVENTION

This invention relates to medical devices, and more particularly, to an apparatus and method for making physiological measurements for diagnostic purposes. The invention has particular application in measuring blood pressure. Specific embodiments of the invention provide automated blood pressure measurement apparatus.

BACKGROUND OF THE INVENTION

Physicians monitor various physiological parameters in their patients and use the results of such monitoring as an important tool to evaluate the patients' health. The monitoring of cardiovascular function is particularly valuable and is performed on a very widespread basis. Accurate measurement of blood pressure and other physiological signals allow for careful diagnosis of medical problems. Monitoring cardiovascular functions, such as blood pressure, can allow a physician to diagnose conditions such as hypertension (increased blood pressure) which may result from processes such as aging or disease.

The heart functions as a pump which moves blood through the circulatory system by a regulated sequence of contractions. The heart ejects blood into the aorta. The blood then flows through the arteries, arterioles, and capillaries to the tissues where the blood delivers oxygen and other nutrients and removes carbon dioxide and other waste products from the tissues. The blood returns to the heart and the lungs where carbon dioxide is expelled from the body and oxygen is again transported into the body. The human body regulates blood pressure throughout the circulatory system to facilitate efficient delivery of blood to the tissues.

Blood pressure does not remain constant but fluctuates during the pumping cycle of the heart. The maximum blood pressure in each cycle is called the systolic blood pressure ("SBP"). SBP occurs as the heart discharges blood into the aorta and the aorta distends to its maximum with the large volume. The minimum blood pressure in each cycle is called the diastolic blood pressure ("DBP"). DBP occurs at the end of the heart's pumping cycle just before the heart begins another contraction. DBP occurs when the aorta has drained of most of the blood from the previous cycle. The mean arterial pressure ("MAP") is the average of the blood pressure throughout a complete cycle. Mean blood pressure is lower further away from the heart in the circulatory system than it is closer to the heart. Mean blood pressure is also subject to hydrostatic pressure variations. Mean blood pressure tends to be reduced at locations above the heart. Mean blood pressure tends to be greater when measured at locations lower than the heart.

Blood pressure also fluctuates with a wide variety of other factors including activity level, pain, temperature, pharmaceutical agents, stress, and recent smoking or food intake. Studies have shown that the measured blood pressure in a single person can vary considerably over time and in different environments. Results of some of these studies are described in the following references: Watson, R. D. S., et al. "*Variation in cuff blood pressure in untreated outpatients with mild hypertension—implications for initiating antihypertensive treatment*" Journal of Hypertension, Vol. 5, No. 2, pp. 207–211 1987; James, G. D., et al. "*The reproducibility of average ambulatory, home. and clinic pressures*" Hypertension, Vol. 11, No. 6, Part 1, pp. 545–549, 1988; and, White, W. B., et al. "*Average daily blood pressure, not office blood pressure. determines cardiac function in patients with hypertension*" Journal of American Medical Association, Vol. 261, No. 6, pp. 873–877, 1989. Blood pressure is also subject to long-term and more permanent changes due to lifestyle, disease and age.

A complication in taking blood pressure measurements accurately is that many patients suffer from a condition known as "white coat hypertension". White coat hypertension is a false hypertension that is normally caused by stress and/or anxiety resulting from the presence of a physician or nurse. Studies of white coat hypertension have shown that up to 21% of untreated borderline hypertensive patients had white coat hypertension. (Pickering, T. G., et al. "*How common is white coat hypertension?*" Journal of American Medical Association, Vol. 259, No. 2, pp. 225–228, 1988 and Staessen et al., "*Antihypertensive treatment based on conventional or ambulatory blood pressure measurement*" Journal of American Medical Association, Vol. 278, No. 13, pp. 1065–1072, 1997.)

White coat hypertension may be reduced with familiarity of the patient with the physician, environment, and/or the technology. For example, it has been shown that the blood pressure readings of patients taken by a physician in a clinical environment on two different days two weeks apart tend to drop with time (James et al., *The reproducibility of average ambulatory, home, and clinical pressures,* Hypertension, Vol. 11, No. 6, Part 1, pp.545–549, 1999).

Various methods are already available for measuring blood pressure. For example, blood pressure may be measured directly in the aorta or other blood vessel. This may be done, for example, by inserting into the blood vessel a probe, such as a needle or catheter which bears, or is attached to, a pressure transducer. The transducer accurately measures the actual pressure of the blood within the blood vessel. Nikolic, U.S. Pat. No. 5,758,652 provides an example of an invasive device capable of making direct blood pressure measurements. The Nikolic device utilizes averaging for smoothing out or removal of respiratory-induced artifacts in an intra-arterial blood pressure signal. Although it is ideal to have directly measured blood pressure values for diagnostic purposes, procedures for directly measuring blood pressure are invasive and are normally restricted to critical care environments such as operating rooms.

Indirect or non-invasive techniques for measuring blood pressure include the traditional method of auscultation in which a blood pressure cuff is inflated to occlude the arteries in the limb (normally the upper arm) and then deflated. During deflation, the physician uses a stethoscope to listen to the Korotkoff sounds (K-sounds) in the blood vessels distal to the blood pressure cuff. The systolic and diastolic pressures are associated with identifiable K-sounds and the cuff pressures at these points are normally measured with a mercury sphygmomanometer. A disadvantage of the auscultation method is that it must be done by a skilled person, such as a physician or nurse.

Another disadvantage of the auscultation method is that it is usually performed by a professional who has limited time. Often only a single measurement is performed. A single measurement may be inaccurate. The American Heart Association recommends that two or more measurements be averaged to produce an accurate determination of blood pressure. Research studies of blood pressure also normally collect multiple readings from patients, and use averaging of the readings in data analysis to limit the effects of fluctuations in pressure and increase accuracy. The measurements should be separated by one to two minutes to allow for release of blood trapped in the veins of the extremity, a wait period that also allows adequate adaptation of the patient to the physician, the environment, and the technology. Making two measurements multiplies the professional time required to obtain a blood pressure measurement.

Barker, U.S. Pat. No. 5,201,320 entitled BLOOD PRESSURE MEASURING DEVICE describes a device designed to address the errors associated with the variability in single blood pressure measurements. The device allows a physician to take two good measurements of blood pressure and to obtain the average of the results automatically. This device requires the physician to use a stethoscope to listen to the K-sounds during automatic deflation of a blood pressure cuff and manually determine the SBP and DBP for each measurement. This device remains subject to the high level of variability and errors associated with white coat hypertension because it requires the presence of a physician or nurse.

The inventors have also conducted unpublished studies which have found that when a series of blood pressure measurements is taken on the same patient the first blood pressure measurement in the series tends to be higher than the values of the other readings. This fact is not generally recognized in the literature and may be explained as results of physical/mental stress experienced by the patients immediately before or during the first blood pressure measurement. The Barker device includes the first blood pressure reading in its average and is therefore less accurate than would be desired.

The prior art includes various devices which automatically take blood pressure measurements by the auscultation method. Such devices typically provide a pressure sensor to measure cuff pressure in place of a mercury manometer, and electronic sound transducers to detect the K-sounds in place of a stethoscope and the trained ear of a physician. Such a device is described in Hutcheson et al., European patent publication No. EP 0-203-181.

Some other automated non-invasive blood pressure measurement systems use an oscillometric technique. In such systems, a blood pressure cuff is inflated to occlude the arteries in the limb (normally the upper arm), and then deflated. During deflation, small oscillations in the cuff pressure are produced by fluctuations in blood pressure in blood vessels underlying the cuff. Pressure transducers accurately measure both the cuff pressure and the small oscillations. Signal processing is then used to determine the SBP, DBP, and MAP from the amplitudes of the oscillations. An oscillometric blood pressure measurement device is described, for example, in Ramsay III U.S. Pat. No. 4,360,029 entitled AUTOMATIC MEAN BLOOD PRESSURE READING DEVICE. This device averages successive pulse oscillations as a noise reduction technique to reduce artifacts and improve pulse pressure measurement accuracy to yield a single MAP reading. More recent prior art devices that implement the oscillometric method are currently used in medicine to provide more accurate measurement of SBP, DBP, and MAP by implementing more advanced signal processing and artifact reduction techniques. Examples of such devices are described in Walloch, U.S. Pat. No. 5,505,206 entitled METHOD AND APPARATUS FOR EXCLUDING ARTIFACTS FROM AUTOMATIC BLOOD PRESSURE MEASUREMENTS and Hersh et al., U.S. Pat. No. 5,590,662 entitled DETECTION OF OSCILLOMETRIC BLOOD PRESSURE COMPLEXES USING CORRELATION. Devices which use oscillometric methods are also subject to the unreliability of a single blood pressure determination. The above-noted AHA recommendations apply to any non-invasive blood pressure methods including manual and automatic auscultation and oscillometry.

Japanese Patent publication No. 63-311929 A discloses an apparatus adapted to acquire and memorize multiple blood pressure measurement values, calculate the average of the values, and display the results selectively by pressing a push button. The device improves measurement accuracy by averaging multiple measurements. However, the device needs to be operated multiple times when multiple measurements are required. When the device is operated by healthcare personnel in a physician's office, errors associated with "white coat hypertension" may still occur.

There exist devices for monitoring blood pressure over time. Such devices typically use one of the above methods to take repetitive measurements of blood pressure and/or other physiological parameters. Such devices do not provide accurate, reliable, single blood pressure readouts for diagnosis of hypertension. The cycle times-for automatic repetitive measurements may be fixed by the developer, programmable by the user, or even random as described in Hutcheson et al. European Patent No. EP 0 203 181 B1. Some monitoring devices designed for long-term collection of physiological data require the physician or user to manually initiate each measurement, as described in Yamaguchi, U.S. Pat. No. 4,747,412 entitled ELECTRONIC SPHYGMOMANOMETER WITH GRAPHICAL OUTPUT.

These automatic long term monitoring devices normally contain memory for storage of data, which can be displayed after a period of data collection and/or transferred to other devices for statistical analysis. Monitoring devices used in critical care environments normally have alarms that will detect if physiological parameters move into dangerous levels and then notify the physician. Prior art monitoring devices, such as the devices described in Titus, U.S. Pat. No. 4,404,974 entitled METHOD AND APPARATUS FOR MONITORING AND DISPLAYING HEART RATE AND BLOOD PRESSURE PRODUCT INFORMATION and Oka et al., U.S. Pat. No. 5,836,887 entitled PHYSICAL INFORMATION MONITOR SYSTEM HAVING MEANS FOR DETERMINING REFERENCE RANGE FOR ABNORMALITY DETERMINATION, BASED ON MOVING AVERAGE OF PREVIOUSLY OBTAINED VALUES typically utilize repetitive measurements and signal processing methods such as smoothing or running average filtering to produce trends in the physiological signals and to accurately detect potentially harmful changes in the signals during long-term monitoring. Such devices are not functionally suited for use in primary care facilities such as doctors' offices.

In summary, prior art devices that make a single blood pressure measurement are subject to errors associated with white coat hypertension and the natural variability in normal blood pressure regulation. Errors in blood pressure measurement may lead to misdiagnosis of significant health issues such as hypertension. Misdiagnosis of hypertension may lead to increased risk to the patient through misclassification and improper prescription of treatment and to increased liability of the physician. None of the prior art devices described above address the problem that the first measurement in a series of measurements tends to be unreliable.

There is a need for devices which can be used in primary care facilities for accurately measuring blood pressure and/ or other physiological parameters. There is a particular need for such devices which can minimize the effects of white coat hypertension and the unreliability of first measurements.

SUMMARY OF THE INVENTION

This invention addresses the problems caused by the fact that the process of measuring values of physiological parameters can affect the values being measured. The invention provides methods and apparatus which provide for the automatic taking of a sequence consisting of a predetermined number of measurements of values for a physiological parameter. A best estimate of the value of the physiological parameter is then obtained from the values obtained from the sequence of measurements. This provides the advantage that the best estimate is likely to be more accurate than a single measurement. Because the apparatus operates automatically it is unnecessary for a physician or other personnel to be present while the sequence of measurements is being made. This both saves operating costs and reduces the possibility that the presence of a physician or other person might influence the measured values of the physiological parameter.

Preferred embodiments of the invention do not use a value obtained in a first measurement of the sequence. As the first measurement is taken a patient becomes familiar with the measuring process which may involve, for example, the inflation of a cuff surrounding the patient's arm. By the time the second measurement is made the patient is somewhat familiar with the measurement process and so the measurement process itself is less likely to affect the values of the physiological parameter(s) being measured.

Most preferably each sequence consists of taking 5 to 7 measurements beginning at times separated from one another by a time in the range of 1 to 5 minutes.

Further aspects and advantages of the invention are set out below.

BRIEF DESCRIPTION OF THE DRAWINGS

In drawings which illustrate specific embodiments of the invention, but which should not be construed as restricting the spirit or scope of the invention in any way.

DETAILED DESCRIPTION

Figure 1:
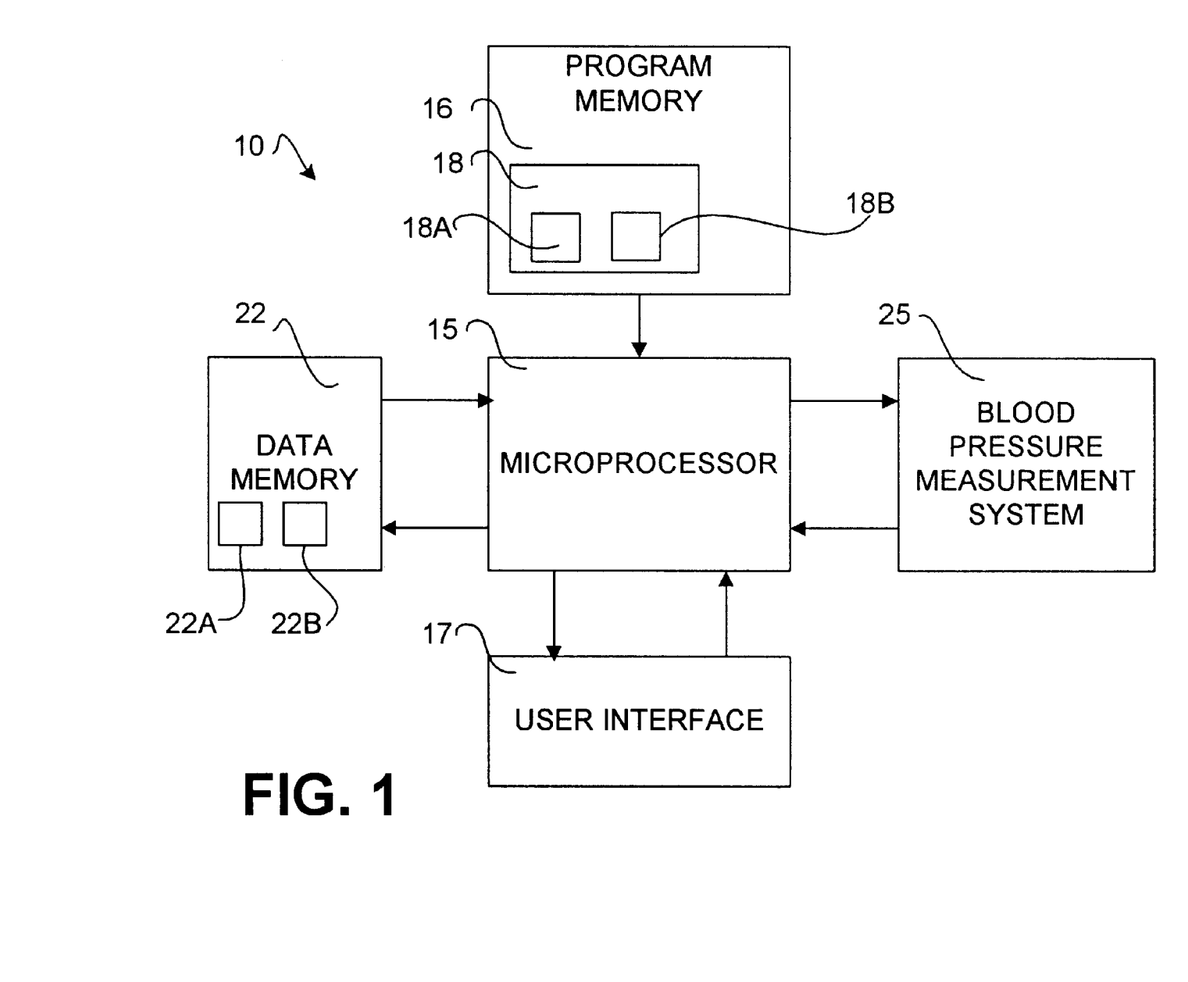
FIG. 1 is a functional block diagram of apparatus according to the invention.

This invention provides an automated apparatus for the measurement of blood pressure or other physiological parameters. FIG. 1, is a functional block diagram of a blood pressure measuring apparatus 10 according to a presently preferred embodiment of the invention. Apparatus 10 comprises a microprocessor 15 which has access to a program memory 16 within which is stored a software program 18 which regulates the operation of apparatus 10. Program memory 16 is preferably a non-volatile memory such as a ROM. Microprocessor 15 is also connected to a data memory device 22 wherein microprocessor 15 can store data, including intermediate results, during execution of software program 18. Data memory device 22 may be any suitable data storage medium including a RAM, a disc drive, or another practical device for storing data.

A blood pressure measurement subsystem 25, as described in detail below with reference to FIG. 2, acts under the control of software 18A which runs on microprocessor 15. Blood pressure measurement subsystem 25 preferably acquires and provides to microprocessor 15 values measured for SBP, DBP, heart rate and a result code which indicates the integrity of the measured values of each of these physiological parameters. Apparatus 10 has a user interface 17, a possible embodiment of which is described in detail below with reference to FIG. 4, which permits a user to set an operating mode for apparatus 10 (in cases where there is more than one operating mode) and which allows a user to initiate a sequence of measurements and displays the results of measurements made by apparatus 10.

Figure 2:
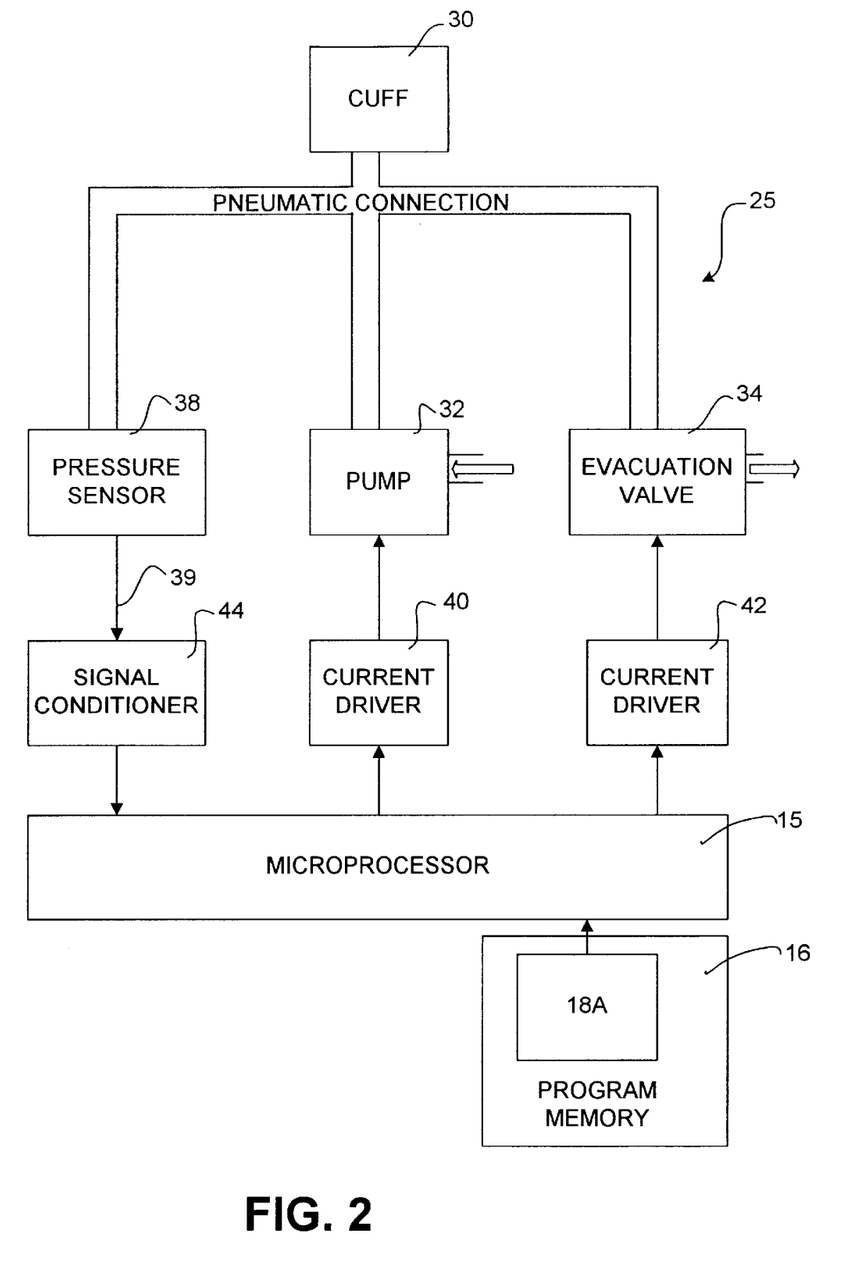
FIG. 2 is a functional block diagram of a blood pressure measurement subsystem, suitable for use in apparatus according to the invention.

FIG. 2 shows a functional block diagram of blood pressure monitoring subsystem 25 and its interface with microprocessor 15 according to a presently preferred embodiment of the invention. Blood pressure measurement subsystem 25 comprises: a blood-pressure cuff 30 which may be inflated to occlude the arteries in a limb of a patient; and a source of a pressurized gas or fluid, such as an electrically-operated pump 32, which is pneumatically connected to cuff 30 to inflate cuff 30 under the control of microprocessor 15. An electrically controlled evacuation valve 34 is pneumatically connected to cuff 30. Cuff 30 can be controllably deflated by opening evacuation valve 34 under the control of microprocessor 15. A pressure sensor 38 is also pneumatically connected to cuff 30. Pressure sensor 38 provides a signal 39 representing a pressure within cuff 30 to microprocessor 15.

Blood pressure measurement subsystem 25 includes suitable interfaces between microprocessor 15 and pump 32, evacuation valve 34 and pressure sensor 38. In the illustrated embodiment, a current driver 40 allows microprocessor 15 to turn pump 32 on or off under the control of software 18A. A current driver 42 allows microprocessor 15 to open or close evacuation valve 34 under control of software 18A. A signal conditioner/pre-amplifier 44 amplifies and removes noise from signal 39 produced by pressure sensor 38 and converts signal 39 to digital form so that microprocessor 15 can read instantaneous pressure within cuff 30.

Software 18A, which is stored in program memory 16, coordinates the operation of pump 32, evacuation valve 34 and takes measurements of signal 39. Software 18A then computes blood pressure using the well-documented oscillometric technique. One method which may be used to measure blood opressure by the oscillometric technique is described in U.S. Pat. No. 5,355,890 to Aguirre et al. which is incorporated herein by reference. Preferably software 18A also determines whether the computed blood pressure values may be unreliable because of the absence of a signal 39, the presence of noise or apparent artifacts in signal 39 and so on. Techniques for assessing the reliability of a computed blood pressure value are well known to those skilled in the art and will therefore not be further described herein.

Figure 3A:
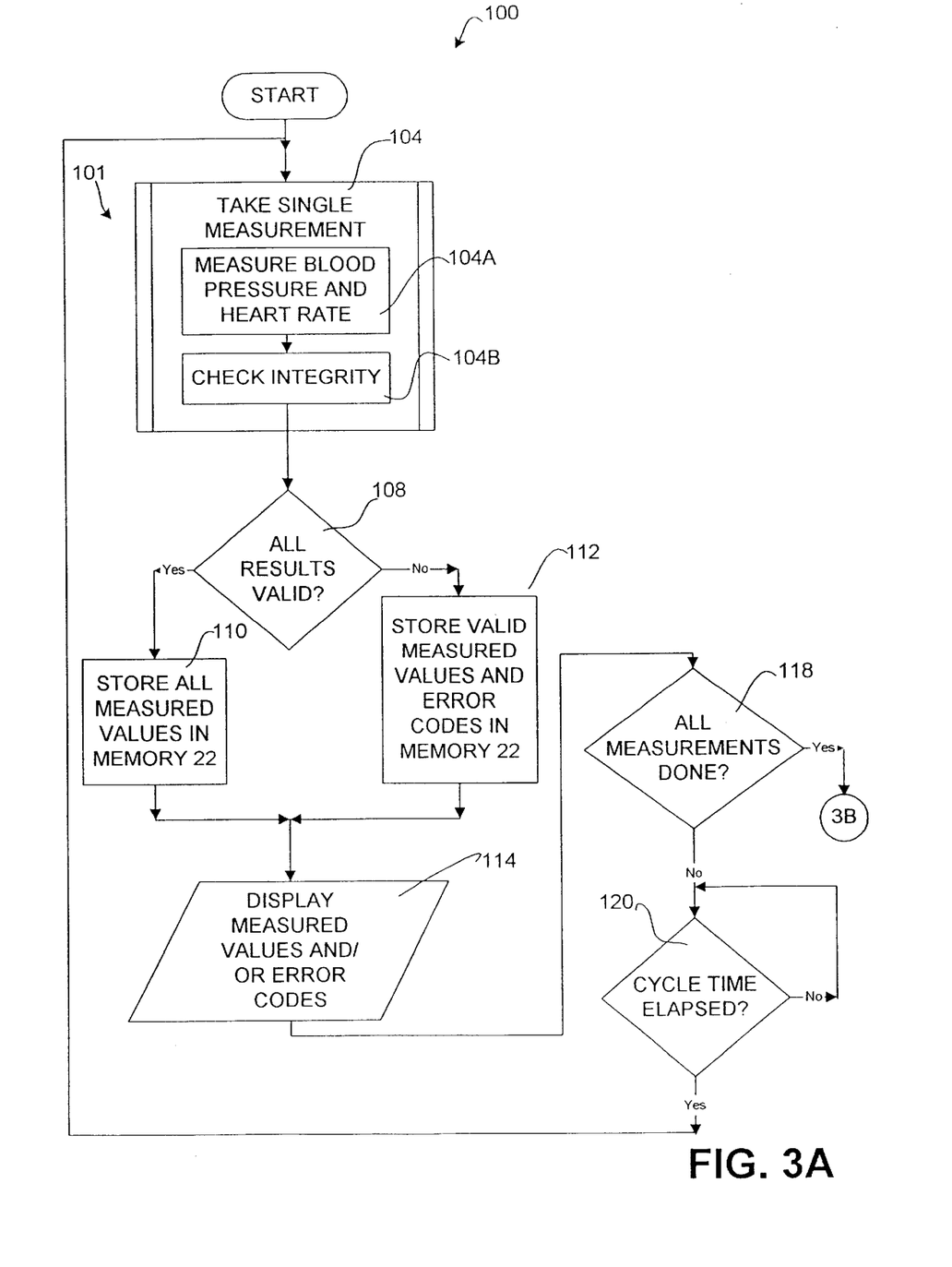
FIGS. 3A and 3B together provide a flow chart representing, at a high level, a program control algorithm by which a microprocessor can coordinate a sequence of blood pressure measurements according to the invention.
Figure 3B:
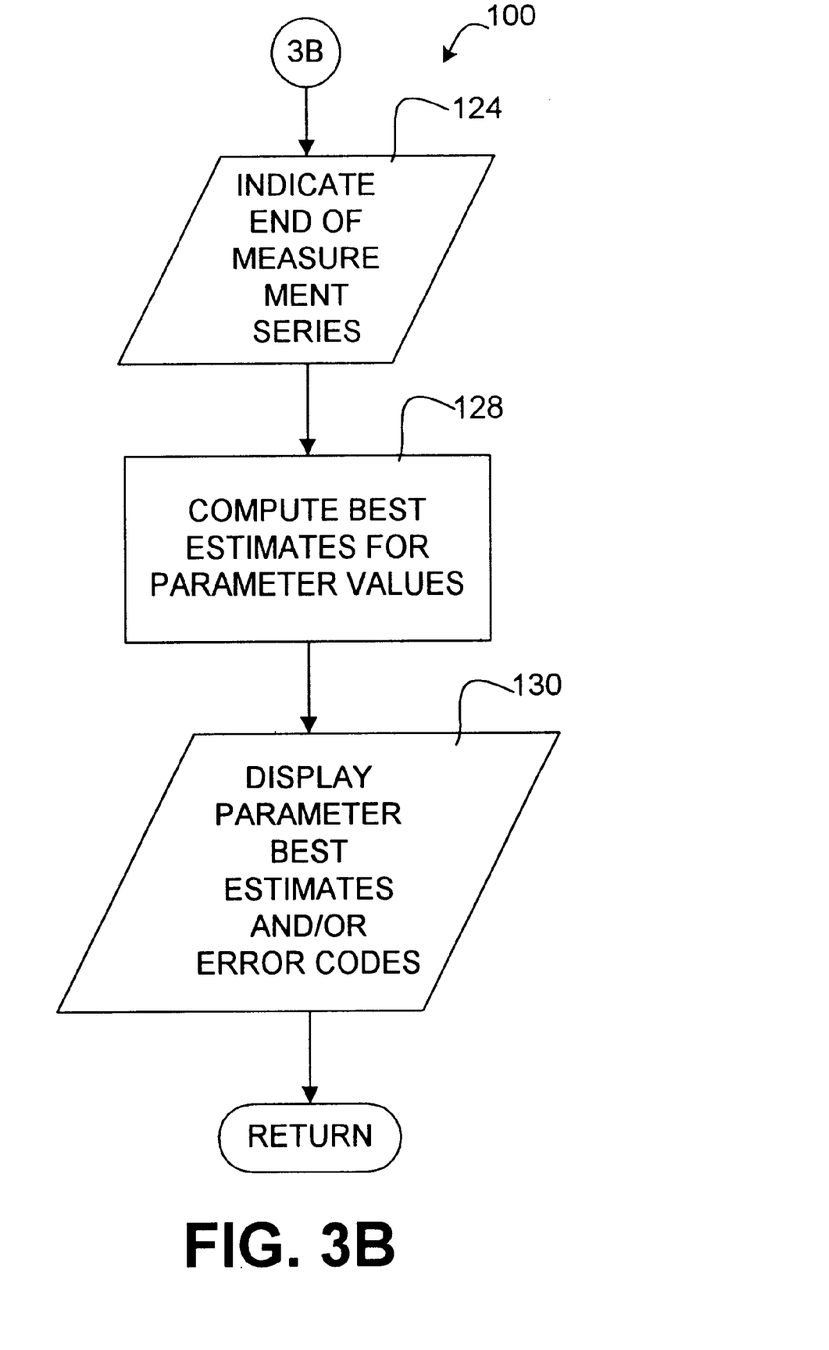

FIGS. 3A and 3B are a flow chart which illustrates high level steps in a method 100 for determining blood pressure and heart rate according to a currently preferred embodiment of the invention. Method 100 automatically takes a sequence at least three blood pressure measurements. Most preferably each sequence consists of 5–7 measurements. The number of measurements taken in method 100 may be set, for example, it may be provided by a static value stored in program memory 16 but is preferably user selectable.

The cycle time, which is the time between the starts of consecutive measurements in a measurement sequence, is preferably in the range of 1 to 5 minutes. The cycle time in method 100 may be set, for example it may be determined by a static value stored in program memory 16, but is preferably user selectable.

Method 100 is performed under the control of software 18. Software 18 runs continuously and waits in a "ready mode" until a user indicates via user interface 17 that a blood pressure measurement should be made. While in its ready mode, software 18 monitors user interface 17 and accepts user commands to set operating parameters for apparatus 10. For example, a user may use interface 17 to specify a number of individual blood pressure measurement cycles to be made in each measurement sequence and the time between successive blood pressure measurement cycles. Software 18 also monitors user interface 17 to determine when a user has entered a command to initiate a measurement sequence (or a single measurement cycle).

When a user initiates a blood pressure measurement sequence then software 18 enters a loop 101 in which a desired number of measurements are made. In loop 101 software 18 first invokes software 18A (step 104). Software 18A performs a blood pressure measurement and a heart rate measurement using the oscillometric technique (step 104A). Software 18A also performs a check of the integrity of the determined values of SBP, DBP, and heart rate (step 104B). Software 18A then returns the values measured for SBP, DBP, and heart rate along with a result code. The result code indicates to control software 18 which, if any, of the data values for SBP, DBP, and heart rate are invalid or unreliable, and the reason for the invalidity or unreliability.

The result code may indicate errors that include, but are not limited to the following: SBP is outside of design limits; DBP is outside of design limits; DBP is indeterminate; noise/artifact level exceeds a threshold value; heart rate is outside of design limits; or heart rate is too irregular.

Software 18 determines whether or not the returned result code indicates that reliable values for all of the desired physiological data were successfully obtained (step 108). If so, then all of the data values returned by software 18A are stored in data memory 22 (step 110). Software 18 keeps track of how many successful blood pressure measurements have been made. This may be done, for example, by incrementing one or more records, pointers, and/or counters maintained by software 18.

If software 18 finds a result code in step 108 which indicates that values for some or all of the desired physiological data were not successfully obtained then only successfully obtained data values, if any, are stored in data memory 22 (step 112), and software 18 only updates those pointers and/or counters relevant to the successfully-determined data. The error codes for unsuccessful data are also stored in data memory 22.

In step 114 software 18 causes user interface 17 to display the data values measured in step 104 including SBP, DBP, and HR, or their respective error codes.

Software 18 then determines whether the desired number of measurements has already been made (step 118). This may be done by comparing the contents of a counter which records the number of measurements performed to the contents of a data memory location 22A which contains the desired number of measurements. If the desired number of measurements has not been completed, then software 18 determines whether the desired cycle time has already elapsed (step 120) and then loops back to repeat measurement step 104.

Determining whether the desired cycle time has already elapsed may be done by comparing the contents of a counter, which records the time elapsed, to the contents of the data memory location 22B. Waiting step 120 may involve software 18 performing certain operations a specified number of times, in which case, processor 15 and software 18 constitute a timer. Waiting step 120 could also involve processor 15 triggering, or monitoring an external timer (not shown).

If, on the other hand, all of the desired number of measurements have been completed, then software 18 exits loop 101 and signals the end of the measurement series (step 124), for example, by sounding an audible signal, such as a buzzer.

Next, software 18 invokes a software routine 18B which determines best estimates for SBP, DBP, and heart rate (step 128) based on the data from some or all of the measurement cycles performed. In a presently preferred embodiment of the invention, the best estimate is preferably obtained by averaging successfully determined data values. Most preferably data values obtained during the first measurement cycle are not included in the computation of the best estimate.

The best estimates for each of SBP, DBP, and heart rate are then displayed via user interface 17 (step 130). If software 18B cannot determine a best estimate for any of the physiological parameters, then software 18B returns an alphanumeric error code to be displayed. The error code indicates that there is a problem and preferably indicates the type of problem. The displayed error code preferably consists of letters and numbers, for example "E57" so that it cannot be mistaken for the value of a physiological parameter.

Figure 4:
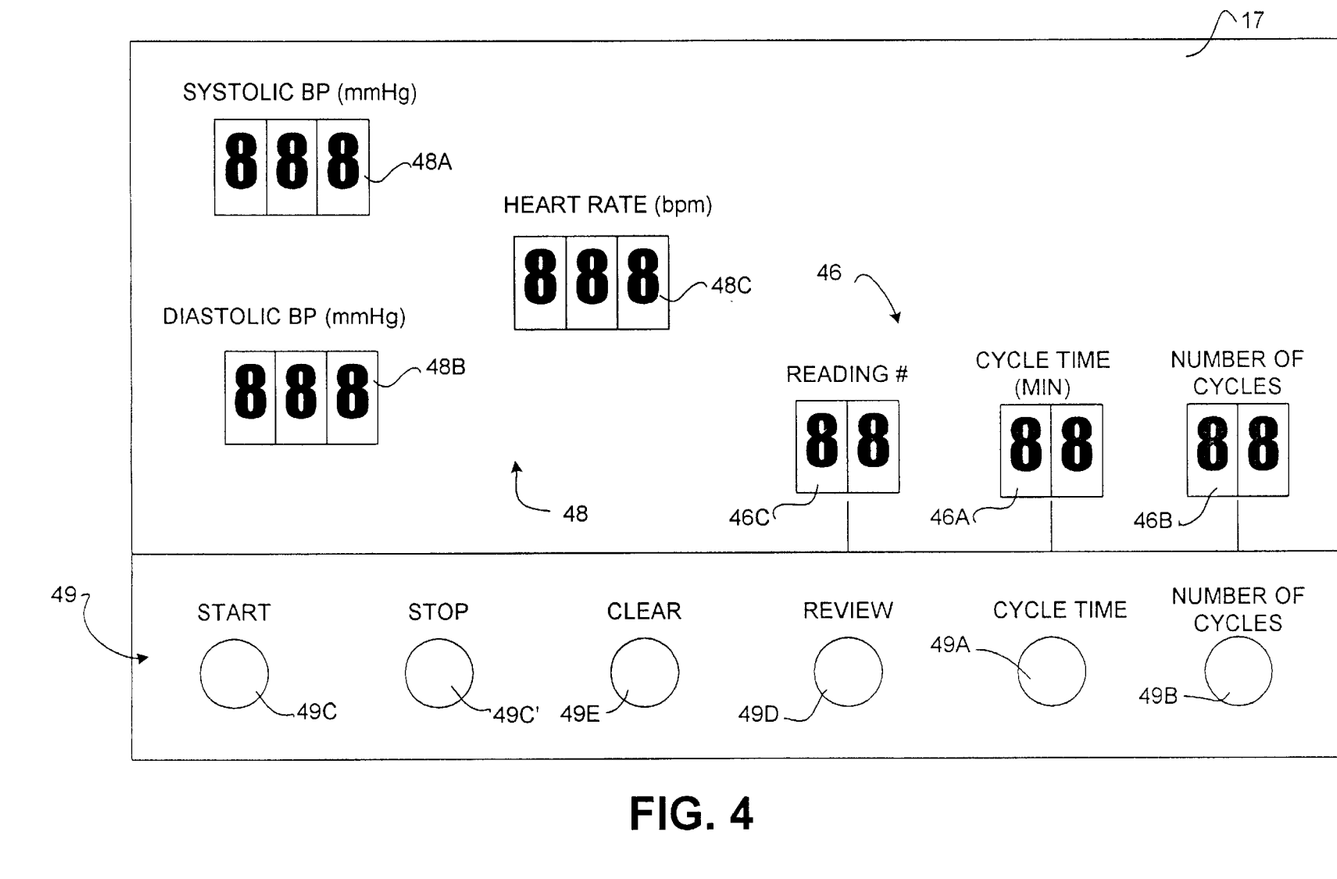
FIG. 4 is a front view of a control panel showing a user interface according to one embodiment of the invention; and, FIG. 5 is a functional block diagram of an alternative embodiment of the invention.

FIG. 4 is a diagram of a user interface 17, according to a presently preferred embodiment of the invention. User interface 17 comprises displays 48 capable of displaying measured values of physiological parameters including SBP, DBP and heart rate or their respective error codes and displays 46 capable of displaying information about the operational status of apparatus 10. User interface 17 also comprises one or more controls 49 for receiving commands from a user. In the illustrated embodiment controls 49 comprise push button switches.

When apparatus 10 is turned on, software 18 begins to run in its "ready mode". A cycle time display 46A indicates the interval, in minutes, between the automatic blood pressure measurement cycles (e.g. the duration of each cycle of loop 101 as controlled by step 120). A user can adjust the cycle time with a cycle time control 49A. A display 46B indicates the number of individual blood pressure measurement cycles which will be performed in each automatic mode sequence. A user can adjust the number of individual measurement cycles in each sequence with a control 49B. Where controls 49A and 49B are pushbuttons, as shown, then the user can vary the interval between successive blood pressure measurements by pressing the cycle time push-button 49A repeatedly to cycle the monitor though the available cycle time options, until the desired cycle time is displayed on cycle time display 46A. The cycle time is automatically updated in data memory location 22B. The user can vary the number of blood pressure measurement cycles in a sequence by pressing the number push-button 49B repeatedly to cycle apparatus 10 though the available number of measurement options, until the desired number of measurement cycles is displayed in display 46B. The number of measurement cycles for each sequence is automatically updated in the data memory location 22A.

A user can initiate a measurement sequence by pressing "star" control 49C. The first measurement cycle (step 104) of the sequence will begin immediately after a user presses control 49C. Preferably a user can terminate a measurement sequence at any time by pressing start control 49C again. In the alternative, interface 17 may provide a separate stop control 49C' as shown in FIG. 4.

Upon completion of each blood pressure measurement cycle, software 18 causes SBP to be displayed on SBP display 48A (if SBP was successfully determined, or if not, an error code indicating the nature of the error). Software 18 causes DBP to be displayed on display 48B (if DBP was successfully determined or, if not, an error code indicating the nature of the error). Software 18 causes heart rate to be displayed on display 48C (if that quantity was successfully determined or, if not, an error code indicating the nature of the error). Display 46C displays the number of the current measurement.

Where the value of a physiological parameter cannot be successfully determined the displayed error codes will indicate, for example: excessive noise; SBP beyond measurement range; DBP not found; heart rate beyond measurement range; heart rate too irregular.

After the completion of the final blood pressure measurement cycle in the automatic sequence provided by loop 101, software 18 invokes software routine 18B which computes a best estimate of SBP, DBP and heart rate from the set of measurements obtained during the sequence. Software 18 then causes the best estimates to be displayed automatically on displays 48. If the best estimate for any of the parameters can not be determined, then a meaningful error code is displayed in that parameter's respective display. As noted above, in a presently preferred embodiment of the invention, the results of measurements made in the first cycle of a sequence is not used in obtaining a best estimate of SBP, DBP and heart rate. It has been found that leaving out the first measurement tends to minimize the effects of "white coat hypertension". In non-preferred embodiments of the invention, results from the first measurement cycle may be included in the analysis.

After a sequence of measurements has been completed then a user can review the results of individual measurements made in each measurement cycle of the sequence by pressing "review" button 49D. When software 18 detects that button 49D has been pressed, software 18 retrieves from data memory 22 and displays on displays 48A, 48B, and 48C, the results of a previous measurement cycle which is identified by the value in display 46C. Repeatedly pressing button 49D causes software 18 to sequentially display the results of each measurement in the cycle, backwards from most recent to earliest. Pressing button 49D when the results of the earliest measurement is being displayed causes software 18 to display the best estimate once again. Values obtained during the first measurement cycle are preferably not displayed in cases where the results of the first measurement cycle are not included in the computation of the best estimates.

Interface 17 provides a "clear" button 49E. By pressing button 49E, a user can cause software 18 to clear the stored physiological data from memory 22 and return to the "ready" mode in preparation for taking another sequence of blood pressure measurements.

Preferably, apparatus 10 can be operated in a "manual" mode wherein pressing the "start" button 49C initiates a single blood pressure measurement cycle.

It can be appreciated that the methods and apparatus of the invention provide a number of advantages over the prior art. Firstly, the apparatus of the invention permits the automatic measurement of a physiological parameter, such as blood pressure, by taking a selected number of measurements separated by desired time intervals and then obtaining a best estimate of the parameter value from the results of two or more measurements. This provides better accuracy than those prior apparatus and methods which take only a single measurement. Secondly, the apparatus of the invention is automatic and can operate without a physician or other medical personnel in attendance. This tends to reduce the effects of "white coat hypertension" and also reduces the costs associated with obtaining measurements. Thirdly, in preferred embodiments, the apparatus makes one or more initial measurements whose values are not counted in determining the best estimate of the parameter value. This permits a patient to become familiar with the way that the apparatus behaves while measurements are being taken. In subsequent measurements the operation of the apparatus tends to affect the patient less than in the first measurement.

As will be apparent to those skilled in the art in the light of the foregoing disclosure, many alterations and modifications are possible in the practice of this invention without departing from the spirit or scope thereof. For example, it is blood pressure and heart rate which are measured in the embodiments of the invention described above. In the alternative the invention could be used to make measurements of other physiological parameters. In the above description blood pressure is determined by the well-documented oscillometric technique. The invention could also be practised by measuring blood pressure according to K-sound techniques, a combination of oscillometric techniques and K-sound techniques, or other blood pressure measurement techniques such as pulse transit techniques. The particular technique for determining blood pressure is not relevant to this invention.

While the above description describes obtaining a best estimate from a plurality of individual measurements of blood pressure by taking an average of the blood pressure values obtained in the individual measurements, the best estimate may also be obtained by taking the median value of successfully-determined blood pressure values or by taking a weighted average of successfully-determined blood pressure values or by using other statistical methods such as optimum estimation methods.

Where best estimates are obtained by using a weighted average it is preferable to apply higher weights to the most recent measurements. This is to take advantage of the natural settling of blood pressure with successive blood pressure measurements. An example of weighting sets for a sequence of 5 readings is (0.10, 0.15, 0.20, 0.25, 0.30).

User interfaces of many kinds may be used with the invention. The user interface 17 described above is by way of example only. All that is necessary is that the user interface provide some way for a user to cause a sequence of measurements to commence and some way for the user to be made aware of the results of the measurements. Preferably the user interface also allows the user to somehow configure apparatus 10 to take a specified number of measurements in each sequence of measurements and to wait for a specified time period between measurements. It would be possible to practice the invention with an apparatus reconfigured to perform a non-adjustable predetermined number of measurements in each sequence of measurements and to provide a non-adjustable predetermined waiting period between successive measurements in a sequence of measurements.

Figure 5:
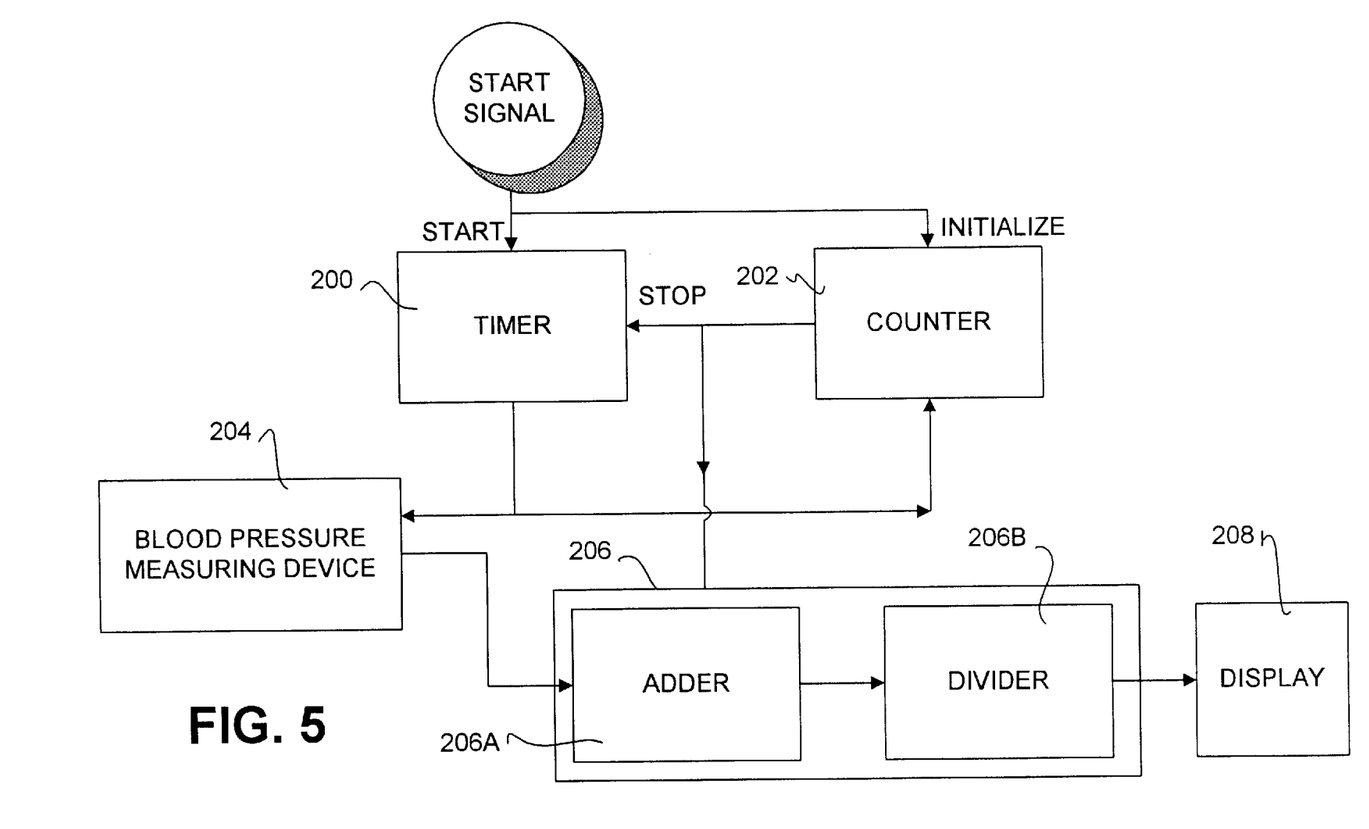

The above description describes apparatus 10 as having a microprocessor 15 which runs software 18 which coordinates the operation of apparatus 10. Microprocessor 15 and software 18 may be termed a "control means" because they together coordinate the operation of apparatus 10. It would be possible to create apparatus according to the invention which is not computer controlled. For example, FIG. 5 shows apparatus according to an alternative embodiment of the invention wherein a timer 200 and a counter 202 control the collection of blood pressure measurements by a blood pressure measurement subsystem 204. In the embodiment of FIG. 5, timer 200 and counter 202 constitute a more rudimentary control means. When timer 200 is started by a user its output causes blood pressure measurement subsystem 204 to commence taking a measurement. Timer 200 periodically triggers subsequent measurements by blood pressure measurement system 204. Blood pressure measurement subsystem 204 forwards the results of each measurement to analyser 206. Counter 202 counts the number of measurements triggered by counter 200. After the desired number of measurements have been made, counter 202 inhibits further operation of timer 200 and signals analyser 206. Analyser 206 has an adder 206A which adds together "N" measured values and a divider 206B which divides the result of the adding operation by "N". The output from divider 206B is displayed on a display 208.

While the invention has been described using the example of software 18 which invokes software 18A and 18B to perform measurements and determine a best estimate for the value of the parameter being measured, other software architectures may be used instead.

Those skilled in the art will appreciate that apparatus according to the invention may be made using any of a wide variety of circuit designs and types. Accordingly, the scope of the invention is to be construed in accordance with the substance defined by the following claims.

We claim:

1. A method for measuring a blood pressure of a subject, the method comprising:
   under automatic control, performing a sequence of four or more measurements of the subject's blood pressure at spaced apart times to obtain four or more measured values for the blood pressure; and,
   computing an estimate of the blood pressure from two or more of the measured values without using an initial group of two or more of the measured values in computing the estimate.

2. The method of claim 1 wherein obtaining each measured value for the blood pressure comprises inflating a cuff surrounding a limb of the subject.

3. The method of claim 2 wherein obtaining a measured value for the blood pressure comprises measuring a pressure in the cuff and using an oscillometric technique to compute blood pressure from the measured pressure in the cuff.

4. The method of claim 1 wherein the sequence consists of from 5 to 7 measurements of the subject's blood pressure.

5. The method of claim 1 comprising receiving user input specifying a user-specified number of measurements to be taken in the sequence wherein performing a sequence of four or more measurements of the subject's blood pressure comprises performing the user-specified number of measurements.

6. The method of claim 4 comprising providing a time interval in the range of 1 minute to 5 minutes between the starts of successive blood pressure measurements in the sequence.

7. The method of claim 1 comprising providing a time interval in the range of 1 minute to 5 minutes between the starts of successive blood pressure measurements in the sequence.

8. The method of claim 1 comprising, before performing the sequence of measurements, accepting a user input specifying a time interval between the starts of successive blood pressure measurements in the sequence wherein performing the sequence of measurements comprises providing the user-specified time interval between the starts of successive blood pressure measurements in the sequence.

9. The method of claim 1 wherein computing an estimate of the blood pressure from two or more of the measured values comprises excluding measured values which fail to satisfy an acceptance criterion.

10. The method of claim 1 wherein performing the sequence of measurements comprises comparing a number of completed measurements to a number of measurements specified by a user and the method continues performing the sequence of measurements while the number of completed measurements is less than the number of measurements specified by the user.

11. The method of claim 10 wherein the number of measurements specified by the user exceeds 4.

12. The method of claim 11 wherein the number of measurements specified by the user is in the range of 5 to 7.

13. A method for measuring a blood pressure of a subject, the method comprising:
   under automatic control, performing a sequence comprising a number of cycles at spaced apart times, each cycle comprising one or more physical actions and, during at least two of the cycles, recording measured values of the subject's blood pressure;
   computing an estimate of the blood pressure from two or more of the measured values without using any measured values obtained during an initial one or more of the cycles in computing the estimate.

14. The method of claim 13 wherein the physical actions comprise inflating and deflating an inflatable member.

15. The method of claim 14 wherein the inflatable member comprises a cuff on a limb of the subject.

16. The method of claim 14 wherein recording measured values of the subject's blood pressure comprises making an oscillometric measurement of the subject's blood pressure.

17. The method of claim 16 wherein the inflatable member comprises a cuff on a limb of the subject and the physical actions comprise inflating and deflating the cuff.

18. The method of claim 17 wherein the number of cycles is predetermined.

19. The method of claim 16 wherein computing the estimate of the subject's blood pressure is performed without using any measured values obtained during an initial group of two or more of the cycles.

20. The method of claim 16 wherein calculating the estimate of the subject's blood pressure comprises computing an average of a plurality of the two or more of the measured values.

21. The method of claim 16 wherein calculating the estimate of the subject's blood pressure comprises computing a weighted average of a plurality of the two or more of the measured values.

22. The method of claim 21 comprising weighting more recently obtained ones of the plurality of the two or more of the measured values more heavily than less recently obtained ones of the plurality of the two or more of the measured values.

23. The method of claim 16 wherein calculating the estimate of the subject's blood pressure comprises computing a median of a plurality of the two or more of the measured values.

24. The method of claim 16 comprising providing a time interval in the range of 1 minute to 5 minutes between the starts of successive cycles in the sequence of cycles.

25. The method of claim 16 wherein the sequence consists of from 5 to 7 measurements of the subject's blood pressure.

26. The method of claim 13 wherein the method comprises
receiving a user input and determining a total number of cycles from the user input;
comparing a number of completed cycles to the total number of cycles; and,
continuing to perform the sequence while the number of completed cycles is less than the total number of cycles.

27. The method of claim 13 wherein computing the estimate of the subject's blood pressure is performed without using any measured values obtained during an initial group of two or more of the cycles.

28. The method of claim 13 comprising, before performing the sequence of cycles, receiving user input specifying a user-specified number of cycles to perform wherein performing the sequence of cycles comprises performing the user-specified number of cycles.

29. The method of claim 13 comprising providing a time interval in the range of 1 minute to 5 minutes between the starts of successive cycles in the sequence of cycles.

30. The method of claim 13 comprising, before performing the sequence of cycles, accepting a user input specifying a time interval between the starts of successive cycles in the sequence wherein performing the sequence of cycles comprises providing the user specified time interval between the starts of successive cycles in the sequence.

31. The method of claim 13 comprising leaving the subject alone in a room while the blood pressure measurement device is performing the sequence of cycles.

32. The method of claim 13 wherein calculating the estimate of the subject's blood pressure comprises computing an average of a plurality of the two or more of the measured values.

33. The method of claim 13 wherein calculating the estimate of the subject's blood pressure comprises computing a weighted average of a plurality of the two or more of the measured values.

34. The method of claim 15 comprising weighting more recently obtained ones of the plurality of the two or more of the measured values more heavily than less recently obtained ones of the plurality of the two or more of the measured values.

35. The method of claim 13 wherein calculating the estimate of the subject's blood pressure comprises computing a median of a plurality of the two or more of the measured values.

36. The method of claim 13 wherein computing the estimate of the blood pressure from two or more of the measured values comprises excluding measured values which fail to satisfy an acceptance criterion.

37. The method of claim 13 comprising sounding an audible signal upon completion of the sequence.

38. A method for obtaining a measurement of a subject's blood pressure, the method comprising:

providing a blood pressure measurement device comprising an inflatable member;
placing the inflatable member on a limb of the subject;
causing the blood pressure measurement device to perform a sequence of a number of cycles, the sequence including an initial cycle and a plurality of additional cycles, each of the cycles comprising inflating and deflating the inflatable member and during at least a plurality of the additional cycles recording measurements of the subject's blood pressure;
computing an estimate of the subject's blood pressure from a plurality of the recorded measurements wherein the plurality of measurements does not include a measurement obtained in the initial cycle; and,
performing one or both of displaying the estimate on a display and recording the estimate.

39. The method of claim 38 wherein the inflatable member comprises an inflatable cuff and placing the inflatable member on a limb of the subject comprises surrounding a limb of the subject with the inflatable cuff.

40. The method of claim 38 wherein the plurality of measurements used in computing the estimate of the subject's blood pressure does not include measurements obtained in an initial group of one or more of the additional cycles.

41. The method of claim 38 comprising leaving the subject alone in a room while the blood pressure measurement device is performing the sequence of cycles.

42. The method of claim 38 wherein calculating the estimate of the subject's blood pressure comprises computing an average of a plurality of the recorded measurements.

43. The method of claim 38 wherein calculating the estimate of the subject's blood pressure comprises computing a weighted average of a plurality of the recorded measurements.

44. The method of claim 43 comprising weighting more recently obtained ones of the plurality of recorded measurements more heavily than less recently obtained ones of the plurality of recorded measurements.

45. The method of claim 38 wherein calculating the estimate of the subject's blood pressure comprises computing a median of a plurality of the recorded measurements.

46. The method of claim 38 wherein recording measurements of the subject's blood pressure comprises using an oscillometric method to obtain values representing the subject's blood pressure and recording the values.

47. The method of claim 38 wherein the sequence consists of from 5 to 7 cycles.

48. The method of claim 47 wherein there is a time interval in the range of 1 minute to 5 minutes between the starts of successive cycles in the sequence.

49. The method of claim 38 wherein there is a time interval in the range of 1 minute to 5 minutes between the starts of successive cycles in the sequence.

50. The method of claim 38 comprising, before causing the blood pressure measurement device to perform a sequence of a predetermined number of cycles, receiving user input specifying the predetermined number of cycles.

51. The method of claim 50 wherein the sequence consists of more than 5 cycles.

52. The method of claim 38 wherein the method comprises:
receiving a user input and determining a total number of cycles from the user input;
comparing a number of completed cycles to the total number of cycles; and, continuing to perform the sequence while the number of completed cycles is less than the total number of cycles.

53. The method of claim 38 comprising, after the sequence of cycles has been completed, displaying each of the recorded measurements.

54. The method of claim 38 comprising:
before causing the blood pressure measurement device to perform a sequence of a predetermined number of cycles, receiving user input specifying a time period
wherein causing the blood pressure measurement device to perform a sequence of a predetermined number of cycles comprises causing start times of successive ones of the cycles to be spaced apart by the time period.

55. The method of claim 38 comprising:
receiving a user input and obtaining a desired time between cycles from the user input; and,
initiating an additional cycle when a time since a previous cycle is equal to the desired time between cycles.

56. The method of claim 38 wherein the sequence consists of more than 5 cycles.

57. The method of claim 38 wherein:
recording measurements of the subject's blood pressure comprises recording measured values of each of the subject's systolic blood pressure and diastolic blood pressure;
computing the estimate of the subject's blood pressure comprises computing estimates of the subject's systolic and diastolic blood pressures; and the method comprises:
displaying the estimates of the subject's systolic and diastolic blood pressures on a display.

58. An apparatus for measuring a physiological parameter of a subject, the apparatus comprising:
a measuring means for measuring a value of a physiological parameter;
a controller connected to the measuring means, the controller adapted to cause the measuring means to make a sequence consisting of a number of measurements of the physiological parameter;
a memory for receiving and storing measured values of the physiological parameter;
calculation means for determining an estimate of the physiological parameter from a plurality of the measured values; and,
a display for displaying the estimate;
wherein the controller comprises a timer and a counter, the timer configured to set a time between sequential measurements in the sequence, the counter counting the measurements made by the measuring means; and,
wherein the calculation means calculates the estimate without reference to an initial two or more of the measured values measured by the measuring means.

59. The apparatus of claim 58 wherein the controller comprises a programmed microprocessor.

60. The apparatus of claim 58 wherein the measuring means comprises a blood pressure measuring means and the physiological parameter measured comprises a blood pressure of a subject.

61. The apparatus of claim 60 wherein the measuring means comprises an inflatable member and a pressure sensor for measuring a pressure within the inflatable member.

62. The apparatus of claim 61 wherein the inflatable member comprises an inflatable cuff.

63. The apparatus of claim 60 comprising a user input for receiving the number.

64. The apparatus of claim 60 comprising a user input for receiving a user-specified value wherein the apparatus comprises means for setting the time between sequential measurements in response to the user-specified value.

65. The apparatus of claim 58 wherein the controller comprises means for rejecting measurements made by the measuring means which fail to satisfy an acceptance criterion.

66. The apparatus of claim 59 comprising a program memory holding instructions which, when executed by the microprocessor, cause the microprocessor to:
receive a user input and determine a total number of cycles from the user input;
compare a number of completed cycles to the total number of cycles; and,
continue to perform the sequence while the number of completed cycles is less than the total number of cycles.

67. The apparatus of claim 59 comprising a program memory comprising instructions which, when executed on the microprocessor, causes the microprocessor to receive a user input and obtain a desired time between cycles from the user input; and,
initiate an additional cycle when a time since a previous cycle is equal to the desired time between cycles.

68. The apparatus of claim 58 comprising a user control input connected to the controller, wherein the controller terminates performing the sequence of cycles upon operation of the user control input.

69. The apparatus of claim 58 wherein the controller is configured to display the value of the counter on the display while the controller is causing the measuring means to make a sequence consisting of a number of measurements of the physiological parameter.

70. An apparatus for measuring a blood pressure of a subject, the apparatus comprising:
an inflatable member;
a pump connected to pressurize the inflatable member;
a valve connected to vent the inflatable member;
a pressure sensor connected to detect a pressure within the inflatable member;
a controller connected to the pump and valve, the controller configured to perform a sequence of a predetermined number of cycles, the sequence including an initial cycle and a plurality of additional cycles, each of the cycles comprising operating the pump to inflate the inflatable member and operating the valve to deflate the inflatable member;
a measurement system connected to receive a signal from the pressure sensor, the measurement system configured to compute a value for the subject's blood pressure based upon the signal from the pressure sensor during at least a plurality of the cycles and to record the computed values of the subject's blood pressure in a memory;
a calculation system for determining an estimate of the blood pressure from a plurality of the measured values, the plurality of measured values corresponding to cycles which do not include the initial cycle; and,
a display for displaying the estimate.

71. The apparatus of claim 70 wherein the calculation system is configured to determine the estimate of the blood pressure from a plurality of the measured values, the plurality of measured values all corresponding to cycles other than cycles of an initial group of two or more of the cycles.

72. The apparatus of claim 70 comprising a review control, wherein the controller is configured to display the measured values on the display in response to operation of the review control.

73. A program memory containing a software program the software program comprising instructions which, if executed by a processor in a blood pressure measurement device comprising a display and a blood pressure measurement subsystem, cause the processor to:

control the blood pressure measurement subsystem to take a sequence comprising at least three blood pressure measurements, taken at spaced apart times, to obtain three or more measured values for the blood pressure;

compute an estimate of the blood pressure from two or more of the measured values without using an initial group of one or more of the measured values in computing the estimate; and, display the estimate on the display.

74. The program memory of claim 72 wherein the sequence comprises at least four blood pressure measurements and the instructions cause the processor to compute the estimate without using an initial group of two or more of the measured values.

75. A program memory containing a software program the software program comprising instructions which, if executed by a processor in a blood pressure measurement device comprising a display and a blood pressure measurement subsystem, cause the processor to:

control the blood pressure measurement subsystem to perform a sequence comprising a number of cycles at spaced apart times, each cycle comprising one or more physical actions and, during at least two of the cycles, recording measured values of the subject's blood pressure;

compute an estimate of the blood pressure from two or more of the measured values without using any measured values obtained during an initial one or more of the cycles in computing the best estimate; and, display the estimate on the display.

* * * * *

UNITED STATES PATENT AND TRADEMARK OFFICE
CERTIFICATE OF CORRECTION

PATENT NO. : 6,602,199 B2  Page 1 of 1
DATED : August 5, 2003
INVENTOR(S) : Chen, Yunquan et al.

It is certified that error appears in the above-identified patent and that said Letters Patent is hereby corrected as shown below:

Column 9,
Lines 8-9, is corrected to read:
-- A user can initiate a measurement sequence by pressing "start" control 49C. --

Column 13,
Lines 51-55, is corrected to read:
34. The method of claim 33 comprising weighting more recently obtained ones of the plurality of the two or more of the measured values more heavily than less recently obtained ones of the plurality of the two or more of the measured values.

Columns 17-18,
Lines 17-21, is corrected to read:
74. The program memory of claim 73 wherein the sequence comprises at least four blood pressure measurements and the instructions cause the processor to compute the estimate without using an initial group of two or more of the measured values.

Signed and Sealed this

Twenty-fourth Day of February, 2004

JON W. DUDAS
*Acting Director of the United States Patent and Trademark Office*